(12) United States Patent
Friske et al.

(10) Patent No.: US 9,011,395 B2
(45) Date of Patent: Apr. 21, 2015

(54) DRAINABLE OSTOMY POUCH

(71) Applicant: Hollister Incorporated, Libertyville, IL (US)

(72) Inventors: Timothy A. Friske, Round Lake Beach, IL (US); Eric J. Beckemeyer, Grayslake, IL (US)

(73) Assignee: Hollister Incorporated, Libertyville, IL (US)

( * ) Notice: Subject to any disclaimer, the term of this patent is extended or adjusted under 35 U.S.C. 154(b) by 7 days.

(21) Appl. No.: 13/827,997

(22) Filed: Mar. 14, 2013

(65) Prior Publication Data

US 2013/0253456 A1    Sep. 26, 2013

Related U.S. Application Data

(60) Provisional application No. 61/614,690, filed on Mar. 23, 2012.

(51) Int. Cl.
*A61F 5/44*    (2006.01)
*A61F 5/445*    (2006.01)

(52) U.S. Cl.
CPC .............. *A61F 5/445* (2013.01); *A61F 5/4407* (2013.01)

(58) Field of Classification Search
USPC ........................................................ 604/332
See application file for complete search history.

(56) References Cited

U.S. PATENT DOCUMENTS

| 3,189,253 | A |  | 6/1965 | Mojonnier |  |
|---|---|---|---|---|---|
| 3,523,534 | A |  | 8/1970 | Nolan |  |
| 3,690,320 | A | * | 9/1972 | Riely | 604/333 |
| 3,825,005 | A |  | 7/1974 | Fenton |  |
| 4,411,659 | A |  | 10/1983 | Jensen et al. |  |
| 4,988,343 | A |  | 1/1991 | Ballan |  |
| 5,968,024 | A |  | 10/1999 | Freeman |  |
| 6,336,918 | B1 |  | 1/2002 | Olsen et al. |  |
| 6,589,221 | B1 |  | 7/2003 | Olsen et al. |  |
| 6,726,667 | B2 |  | 4/2004 | Leise, Jr. et al. |  |
| 6,780,172 | B2 |  | 8/2004 | Olsen et al. |  |
| 6,887,222 | B2 |  | 5/2005 | Mandzij et al. |  |
| 7,306,581 | B2 |  | 12/2007 | Falconer et al. |  |
| 7,722,585 | B2 |  | 5/2010 | Falconer et al. |  |
| 7,879,015 | B2 |  | 2/2011 | Villefrance et al. |  |
| 7,879,016 | B2 |  | 2/2011 | Mandzij et al. |  |
| 8,672,907 | B2 | * | 3/2014 | Friske et al. | 604/335 |
| 2003/0028160 | A1 | * | 2/2003 | Leise et al. | 604/334 |
| 2003/0073962 | A1 | * | 4/2003 | Olsen et al. | 604/327 |
| 2003/0153882 | A1 | * | 8/2003 | Mandzij et al. | 604/334 |
| 2003/0167042 | A1 | * | 9/2003 | Poulsen | 604/327 |

(Continued)

FOREIGN PATENT DOCUMENTS

EP    2002810 B1    12/2008
EP    1750628 B1    2/2011

(Continued)

OTHER PUBLICATIONS

International Search Report and Written Opinion filed in connection with PCT/US2013/033087 dated Jun. 24, 2013.

*Primary Examiner* — Tatyana Zalukaeva
*Assistant Examiner* — Guy K Townsend
(74) *Attorney, Agent, or Firm* — Levenfeld Pearlstein, LLC

(57) ABSTRACT

A drainable ostomy pouch includes a closure system, which includes four closure members and a two-part fastening system. The closure system is arranged on a neck portion of the drainable pouch, and configured such that the pouch can be securely sealed after the neck portion is folded up three times and closed using the two-part fastening system.

19 Claims, 4 Drawing Sheets

(56) References Cited

U.S. PATENT DOCUMENTS

| | | |
|---|---|---|
| 2005/0117775 A1 | 6/2005 | Wendt |
| 2005/0131360 A1* | 6/2005 | Villefrance et al. ......... 604/332 |
| 2006/0015079 A1* | 1/2006 | Mandzij et al. ............. 604/317 |
| 2007/0265588 A1* | 11/2007 | Pedersen ..................... 604/337 |
| 2008/0051743 A1* | 2/2008 | Falconer et al. ............. 604/332 |
| 2009/0043271 A1* | 2/2009 | Winther ....................... 604/332 |
| 2011/0028924 A1 | 2/2011 | Murray |
| 2011/0144601 A1 | 6/2011 | Villefrance et al. |
| 2012/0022478 A1 | 1/2012 | Friske et al. |

FOREIGN PATENT DOCUMENTS

| | | |
|---|---|---|
| EP | 1033951 B1 | 9/2011 |
| GB | 2268065 A | 1/1994 |
| GB | 2388322 B | 12/2003 |
| GB | 2346328 B | 12/2008 |
| WO | 9925278 A1 | 5/1999 |
| WO | 03065944 A1 | 8/2003 |
| WO | 03086250 A1 | 8/2003 |
| WO | 2005117775 A1 | 12/2005 |

\* cited by examiner

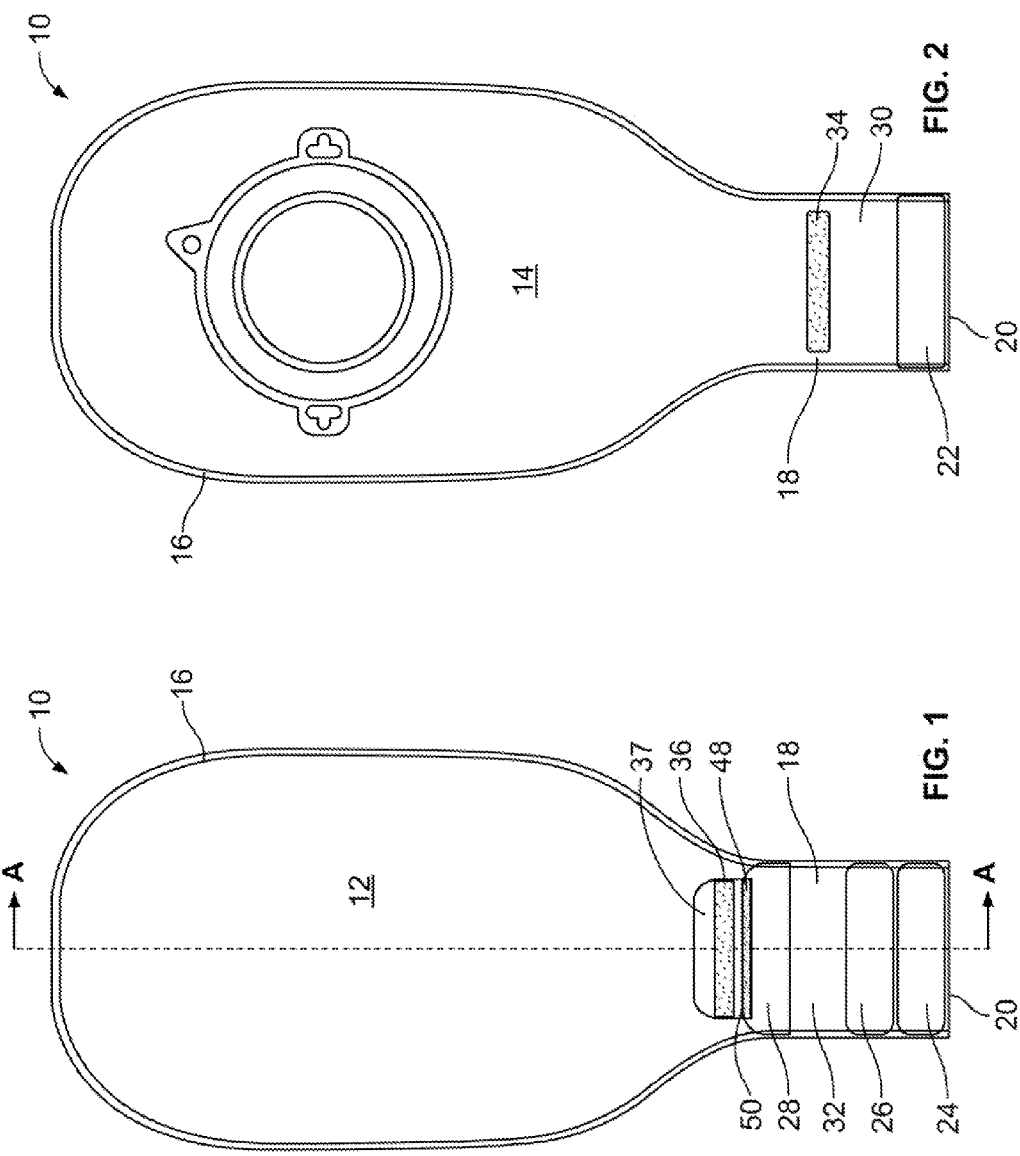

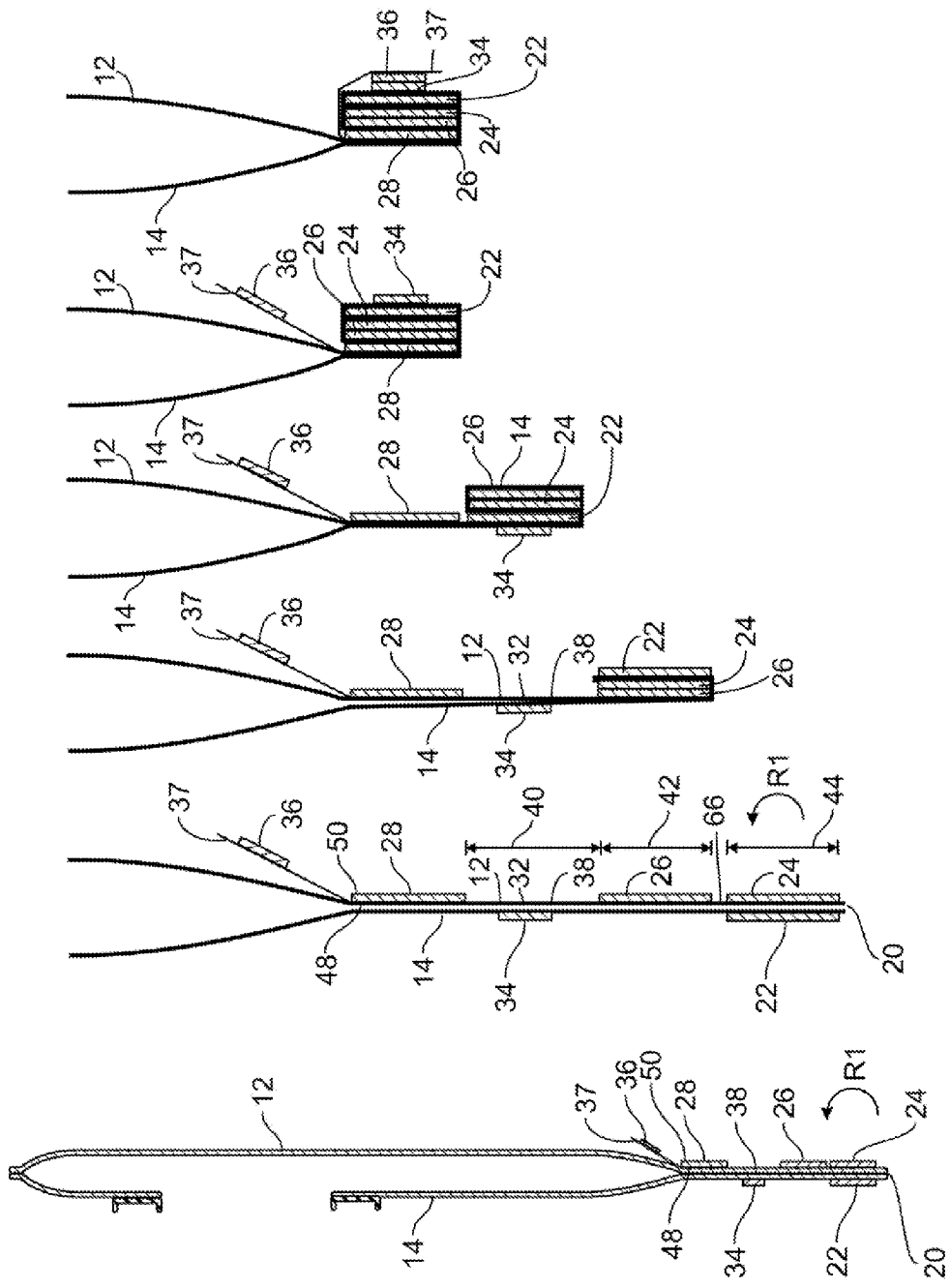

176° TYPICAL BEND

DRAINABLE OSTOMY POUCH

CROSS-REFERENCE TO RELATED APPLICATION. DATA

This application claims the benefit of priority of Provisional Patent Application Ser. No. 61/614,690, filed Mar. 23, 2012 entitled, "DRAINABLE OSTOMY POUCH."

BACKGROUND

The present disclosure generally relates to ostomy appliances, and more particularly to drainable ostomy pouches having closure systems.

Ostomy pouches for collecting body waste are used by patients who have had surgery such as a colostomy, ileostonty, or urostomy. Ostomy pouches typically include flat, opposing side walls secured together along their edges to define a collection cavity. One of the side walls is provided with an opening to receive a stoma, and means to secure the pouch to the user, such as an adhesive barrier, so that body waste discharged through the stoma is received within the cavity.

The ostomy pouch may be a closed-end pouch for a single use, in which case the entire pouch is discarded after it has been substantially filled with stomal discharge. Alternatively, the ostomy pouch can be a drainable pouch with as discharge opening at its lower end, which may be closed during collection of body waste material but may be opened for draining, body waste material from the pouch after a period of use. Such drainable pouches are disclosed, for example, in Nolan, U.S. Pat. No. 3,523,534, and Jensen et al., U.S. Pat. No. 4,411,659, which are incorporated herein in their entirety by reference.

The discharge opening of drainable pouches is typically defined at the end of a narrowed neck portion, which is provided with closure means for maintaining the discharge opening in a sealed condition until waste material is to be drained from the pouch. The closure means may take the form of a clamp, as in the aforementioned Nolan patent, or a device such as conventional wire ties or wraps for securing the neck portion in an upwardly-rolled condition.

For quality of life of the users, drainable pouches should be easy to drain without risking soiling of clothes or the surroundings. They also should be easy to close securely after being drained and amenable to being cleaned after drainage and before closing again, such that the risk of unpleasant odor is substantially reduced. Most importantly, the closure means should provide a secure seal when closed to minimize the risk of leakage.

Many different solutions concerning the closing, cleaning and drainage operations have been proposed and implemented. For example, Villefrance et al., U.S. Pat. No. 7,879,015 and U.S. patent application Ser. No. 12/843,457, which are commonly assigned with the present application and incorporated herein in their entirety by reference, disclose drainable pouches having integral closure systems. For obvious reasons, fluffier improvements in the closure systems for easier operation and reduced risk of leakage are much desired by users.

Accordingly, there is a need for an improved closure system for drainable pouches.

BRIEF SUMMARY

A drainable ostomy pouch including a closure system comprising four closure members and a two-part fastening system is provided according to various embodiments. Such a closure system provides improved sealing properties to reduce the risk of leakage during use.

In one aspect, a drainable ostomy pouch including a closure system is provided. The drainable pouch includes a bodyside wall and an outer wall joined along their peripheral edges to define a cavity therebetween for collecting stomal discharge, and a downwardly extending neck portion terminating in a discharge opening for draining stomal discharge contents collected in the cavity. The neck portion includes a closure system, which includes a first closure member, a second closure member, a third closure member, and, a fourth closure member. The first closure member and the second closure member are arranged on opposite sides of the neck portion, and the third closure member is arranged adjacent to the second closure member, such that the first closure member, the second closure member, and the third closure member are stacked on top of each other after the neck portion is folded once. The fourth closure member is arranged longitudinally offset from the third closure member. The closure system further includes a two-part fastening system comprising a first fastener strip and a second fastener strip.

In one embodiment, each the first closure member and the second closure member is curved smoothly and outwardly relative to the neck portion, such that the discharge opening remains open when neck portion is in a rolled-out position. Further, the third closure member is curved smoothly and outwardly relative to the neck portion. The first closure member is attached on the bodyside wall of the neck portion and the second member is attached on the outer wall of the neck portion. Preferably, the first closure member and the second closure member are configured having similar dimensions, and arranged in a back-to-back relation proximate the discharge opening. The third closure member can also be configured similarly to the first closure member and the second closure member with similar dimensions. The third closure member is attached on the outer wall of the neck portion and longitudinally above the second closure member relative to the discharge opening, in which the second closure member and the third closure member are spaced apart with a first gap therebetween.

In some embodiments, the fourth closure member is also curved smoothly and outwardly relative to the neck portion. The fourth closure member is attached on the outer wall of the neck portion and longitudinally above the third closure member relative to the discharge opening. In such an arrangement, the third closure member and the fourth closure member are spaced apart with a second gap therebetween. A longitudinal width of the second gap is equal to or greater than a longitudinal width of the first, second or third closure member, whichever is largest.

The first fastener strip is attached on the bodyside wall of the neck portion opposite the second gap between the third and fourth closure members. The second fastener strip is disposed on the outer wall of the neck portion and longitudinally above the fourth closure member relative to the discharge opening, such that the first, second and third closure members, and the first fastener strip are arranged along the neck portion between the second fastener strip and the discharge opening. The second fastener strip is arranged on a support member formed of a polymeric film, a portion of which is heat sealed to the outer wall of the neck portion. The fourth closure member is adhesively attached to the outer wall of the neck portion, such that a transversely extending edge of the fourth closure member overlaps the heat sealed portion of the support member.

The neck portion including the closure system is configured to be folded three times and sealed with the two-part fastening system. Further, the neck portion is configured such that the second closure member and the third closure member directly abut each other after the neck portion is folded once, and the first, second, and third closure members are stacked on top of each other. Further, the lust fastener strip, the first closure member, the second closure member, and the third closure member are stacked on top of each other after the neck portion is folded twice. Alter the neck portion is folded three times, the first closure member, the second closure member, the third closure member, the fourth closure member, and the first fastener strip are stacked on to of each other.

In another aspect, a closure system for a drainable ostomy pouch that includes generally parallel sidewalls of flexible sheet material joined along their peripheral edges to define a cavity therebetween for collecting stomal discharge is provided. The drainable ostomy pouch has a downwardly extending neck portion terminating in a discharge opening, on which the closure system is arranged. The closure system includes a first closure member, a second closure member, a third closure member, a fourth closure member, and a two-part fastening system comprising a first fastener strip and a second fastener strip. The first closure member, the second closure member, the third closure member, the fourth closure member, and the first fastener strip are arranged along the neck portion longitudinally between the second fastener strip and the discharge opening. The closure system is configured such that the neck portion is rolled up by folding three times and closed using the two-part fastening system.

In one embodiment, the first closure member, the second closure member, and the third closure member may be formed of the same material having the same thickness, and similar dimensions. The first closure member and the second closure member are attached to different sidewalls of the neck portion and arranged in a back-to-back relation. The third closure member is arranged longitudinally offset from the first closure member and the second closure member with a gap therebetween. In embodiments where the first closure member, the second closure member, and the third closure member have the same longitudinal width, and the fourth closure member is arranged longitudinally offset from the second closure member with a gap therebetween, the gap has a longitudinal width greater than the longitudinal width of the first, second and third closure members. Preferably, the closure system is configured such that the second closure member and the third closure member directly abut each other when the neck portion is rolled up and closed with the two-part fastening system.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings wherein:

FIG. 1 is a schematic view illustrating the non-body side of a drainable ostomy pouch according to an embodiment;

FIG. 2 is a schematic view illustrating the bodyside of the drainable ostomy pouch of FIG. 1;

FIG. 4 is a cross-sectional view of the drainable ostomy pouch of FIG. 1 taken along line A-A;

FIG. 5A is a view similar to FIG. 4 showing details of the neck portion including the closure system;

FIG. 5B is a view similar to FIG. 5A after the neck portion has been folded once;

FIG. 5C is a view similar to FIG. 5A after the neck portion has been folded twice;

FIG. 5D is a view similar to FIG. 5A after the neck portion has been folded three times;

FIG. 5E is a view similar to FIG. 5A after the neck portion has been folded three times and secured with a two-part fastening system;

DETAILED DESCRIPTION

Figure 3:
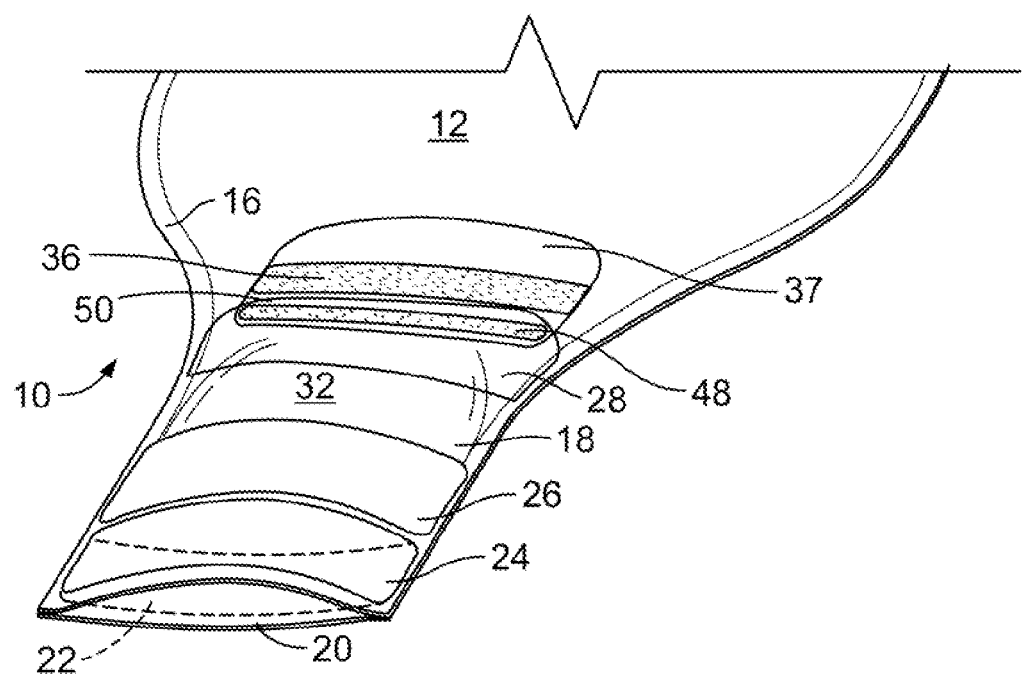
FIG. 3 is an enlarged perspective illustration of a closure system of the drainable ostomy pouch of FIG. 1.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular.

Referring now to the figures, FIGS. 1 and 2 Show a drainable pouch 10 according to an embodiment. The drainable pouch 10 includes an outer wall 12 and a bodyside wall 14, which are joined along their peripheral edges 16 to define a cavil therebetween for collecting stomal discharge. The drainable pouch 10 also has a downwardly extending neck portion 18 terminating in a discharge opening 20 for draining the contents collected in the cavity alter a period of use. The discharge opening 20 of the drainable pouch 10 is closed during use by folding the neck portion 18 upwardly and securing it in the upwardly folded position.

The walls 12, 14 are formed of a suitable flexible sheet material, such as a polymeric film, which can be a monolayer or multilayer film. Each of the walls 12, 14 can be formed of one continuous flexible film to define the entire pouch including the neck portion 18. Alternatively, the walls of the neck portion 18 can be formed of separate flexible films than the walls of the pouch body. That is, the walls of the neck portion 18 may be formed of a different polymeric film than the walls of the pouch body. For example, the polymeric film used to form the walls of the neck portion may be thicker than the polymeric film used to form the walls of the pouch body.

The drainable pouch 10 is provided with multiple closure members 22, 24, 26, and 28 along outer surfaces of the neck portion 18. Each of the closure members is transversely-extending and generally rectangular in its shape, and may be formed by thermal forming extruding, or molding using a suitable polymer material such as, for example, MYLAR® brand polyester (PET) available from DuPont. Further, the drainable pouch 10 is provided with a two-part fastening, system comprising first and second fastener strips 34, 36.

A first closure member 22 is provided on an outer surface 30 of the bodyside wall 14 proximate the discharge opening 20. A second closure member 24, a third closure member 26, and a fourth closure member 28 are arranged on an outer surface 32 of the outer wall 12 along the neck portion 18. Each of the closure members 24, 26 and 28 may have a thickness of about 0.19 mm. The second closure member 24 is arranged proximate the discharge opening 20, such that the first Closure member 22 and the second closure member 24 are in a generally parallel back-to-back relation.

As best shown in FIG. 3, the first and second closure members 22, 24 are each formed such that they are curved smoothly and outwardly relative to the neck portion 18. Since the first and second closure members 22, 24 are arranged on the opposite sides of the neck portion 18 in a back-to-back relation, and each concaves outwardly (that is, they bow away from each other), the first and second closure members 22, 24 do not abut each other when in a rolled-out position, such that de discharge opening 20 remains open. Such arrangement of the first and second closure members 22, 24 also facilitates opening of the discharge opening 20 by the user for emptying of stromal discharge.

The third closure member 26 is located on the outer surface 32 of the outer wall 12 adjacent and generally parallel to the second closure member 24. The second closure member 24 and the third closure member 26 are arranged such that the third closure member 26 is adjacent to and longitudinally offset above the second closure member 24 with relation to the discharge opening 20. Thus, when the neck portion 18 is folded once in the direction of arrow R1 (FIGS. 4-5B), the second closure member 24 abuts the third closure member 26. In the embodiment shown, the first, second and third closure members 22, 24, 26 are formed of the same material and have the same general shape and dimensions. Thus, the third closure member 26 is also curved smoothly and concaves outwardly relative to the neck portion 18. The second closure member 24 and the third closure member 26 may be spaced apart with a gap 66 to allow folding of the neck portion 18, such that the outer surface of the second closure member 24 abuts the outer surface of the third closure member 26 after one fold as shown in FIG. 5B. Alternatively, the second closure member 24 may abut the third closure member 26 when the neck portion 18 is in an unfolded configuration, which creates tension in the film of the outer wall 12 when the neck portion 18 is in a folded configuration.

The fourth closure member 28 is also located on the outer surface 32 of the outer wall 12 generally parallel to the second and third closure members 24, 26. The fourth closure member 28 is arranged longitudinally above the third closure member 26 relative to the discharge opening 211 with a space 38 therebetween. A longitudinal length 40 of the space 38 is at least equal to or greater than a longitudinal length 42 of the third closure member 26 or a longitudinal length 44 of the second closure member 24, whichever is greater, such that when the neck portion 18 is folded fir the second time, the first closure member 22 abuts the outer wall 12 in the space 38 as shown in FIG. 5C. Further, when the neck portion 18 is folded for the third time, the bodyside wall 14 opposite the third closure member 26 abuts the fourth closure member 28 as shown in FIG. 5D.

Further, the neck portion 18 is provided with the first fastener strip 34 on the bodyside wall 14 and the second fastener strip 36, that, as described in further detail below, may be attached to a support member 37 that is in turn attached to the outer wall 12. As illustrated in the drawings, the first and second fastener strips 34, 36 are located at different distances from the discharge opening 20, and they have fastener elements which are adapted for releasable interlocking engagement. The fastener systems associated with the first and second fastener strips 34, 36 can be engaged to secure the folded neck portion as shown in FIG. 5E. In the embodiment shown, the first fastener strip 34 is adhesively attached to the bodyside wall 14 of the neck portion 18 opposite the space 38. Thus, there is no closure strip in a back-to-back relation with the first fastener strip 34. The second fastener strip 36 is arranged longitudinally above the fourth closure member 28 relative to the discharge opening 20. Thus, the first, second, third, and fourth closure members 22, 24, 26, 28, and the first fastener strip 34 are all arranged between the second fastener strip 36 and the discharge opening 20 along the neck portion 18 on either walls 12, 14.

In this embodiment, the second fastener strip 36 is attached to the support member 37 that may be made of a polymeric film, which is heat sealed to the outer wall 12 along a transversely extending peripheral edge 48. The fourth closure member 28 is adhesively attached and partially overlaps the support member 37, such that the heat sealed peripheral edge 48 is under a first transversely extending peripheral edge 50 of the fourth member 28. Such a configuration of the second fastener strip 36 allows for flexible movement of the support member 37 and easy closure of the rolled-up neck portion via the two-part fastening system as shown in FIG. 5E.

The first and second fastener strips 34, 36 may comprise a polypropylene material of the type sold under the trademark DUOTEC by G. Binder GmbH & Co. Holzgerlingen, Germany, which is stated in product literature to work on the principle of interlocking mushroom elements. By using this synthetic material for the first and second fastener strips 34, 36, the discharge opening 20 can be maintained in a closed position absent a disengagement force sufficient to overcome the retention force. Further, the interlocking mushroom elements are designed so both strips can be identical, and thus, there is no need to use physically distinguishable male/female components, or to use any fabric-like material that will have a strong tendency to absorb body waste materials and odors and then be difficult to clean.

Among the attributes for this material are its ability to provide a strong and solid connection when pressed firmly together, its characteristic locking action that provides a user with tactile indication of when the fastener strips are interlocked, and its ability to be repeatedly opened and closed. The opening and closing action of fastener strips formed of this material also produces only very limited noise. However, it is to be understood that other type of fastening means may be used, such as, for example, hook and loop fasteners as marketed under the Velcro trademark or pressure sensitive adhesive coatings.

Figure 6A:
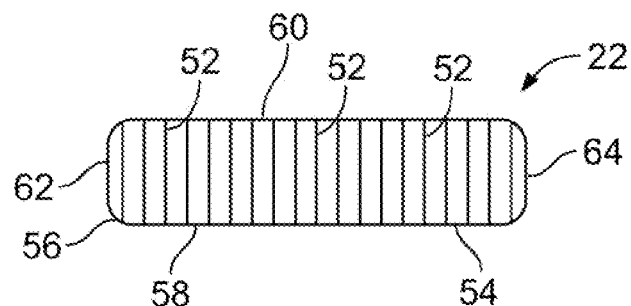
FIG. 6A is a plan view of a curved closure member for a drainable ostomy pouch in accordance with the disclosure.
Figure 6B:
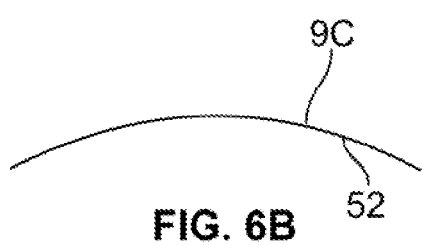
FIG. 6B is a front elevational view illustrating the curvature of the curved, closure member illustrated in FIG. 6A.
Figure 6C:
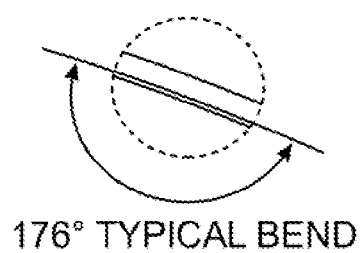
FIG. 6C is a diagrammatic view illustrating a typical bend in each of the multiple bend locations illustrated in FIG. 6A.

Referring to FIGS. 6A-6C, details of the first closure member 22 are shown. The first closure member 22 has a generally rectangular body 54 with rounded edges 56, and includes generally parallel transversely extending edges 58, 60, and generally parallel longitudinally extending edges 62, 64. The first closure member 22 may be on the order of approximately 0.25 mm in thickness. With regard to the transverse dimension, it should be chosen to substantially cover the entire width of the neck portion. The longitudinal dimension of the closure members will typically comprise approximately one quarter the transverse dimension although this can be varied depending upon the various parameters for other components including the width and length of the neck portion.

Referring to FIG. 6A, the first closure member 22 preferably has a plurality of longitudinally extending bends 52. The bends 52 can be evenly spaced across the transverse dimension of the curved spring members, and are preferably spaced apart on the order of approximately 3.5 mm. In addition, each of the bends 52 may be formed at an angle of approximately 176° in order to achieve the desired curvature (FIG. 6C).

More specifically, one manner of obtaining the desired curvature for the first closure member 22 is illustrated in FIG. 6B where the curvature is formed by providing a plurality of typical bends 52 of approximately 176° as illustrated in FIG. 6C. In this embodiment, the second closure member 24 is configured with substantially similar bends 52 to those of the first closure member 22. By forming the first and second closure members 22, 24 with such bends 52, and adhesively attaching them to the neck portion 18 in a back-to-back relation as described above, the closure members will have a natural ability to open the discharge opening 20. When the fastener strips 34, 36 of the two-part fastening system are disengaged and the neck portion 18 is folded downward, the discharge opening 20 is opened by the closure members 22, 24.

As a result, the first and second closure members 22, 24 are normally able to overcome any tendency of the flexible sheet material of the opposite walls 12, 14 of the neck portion to adhere to one another. This facilitates a user's ability to open the neck portion 18 to drain the contents from the cavity of the drainable ostomy pouch 10 as well as to clean immediately inside the discharge opening by forming a natural binge type "coin purse" opening. After cleaning, the neck portion 18 can again be folded up for a secure closure.

In the embodiment shown, the third closure member 26 is configured with substantially similar bends 52 to those of the first and second closure members 22, 24. The third closure member 26 is adhesively attached to the neck portion 18, such that it is arranged longitudinally above the second closure member 24 with its transversely extending edges generally parallel with the transversely extending edges of the second closure member 24. When the third closure member 26 having the concave curvature from the bends 52 is adhesively attached on the neck portion 18, it further facilitates opening of the discharge opening 20. The second closure member 24 and the third closure member 26 are longitudinally separated by a gap 66 of at least equal to the sum of the thicknesses of the second and third closure members to allow the first and second closure members 22, 24 to be folded onto the third closure member 26, so that the closure members 22, 24, 26 all lie flat. Alternatively, the second closure member 24 may abut the third closure member 26 when the neck portion 18 is in an unfolded configuration, which creates tension in the film of the outer wall 12 when the neck portion 18 is in a folded configuration. After one fold, the first, second and third closure members 22, 24, 26 are all stacked on top of each other as shown in FIG. 5B.

Figure 7:
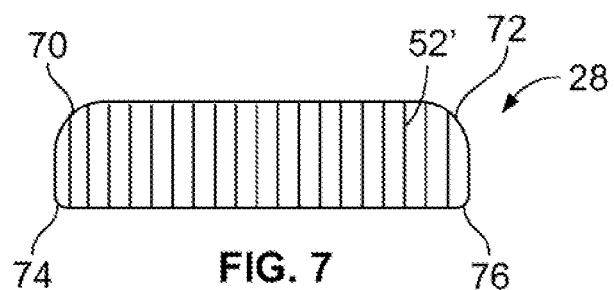
FIG. 7 is a plan view of a fourth closure member of a drainable ostomy pouch in accordance with the disclosure.

The fourth closure member 28 is configured similarly to the first, second and third closure members 22, 24, 26 with multiple bends 52'. However, as shown in FIG. 7, two of the edges 70, 72 of the fourth closure member 28 are rounded with a larger radius than the other edges 74, 76. The fourth closure member 28 is arranged longitudinally offset from the third closure member 26 by space 38, such that its transversely extending edges are generally parallel with the transversely extending edges of the third closure member 26. The fourth closure member 28 is attached to the neck portion 18 such that the rounded edges with smaller radius are closer to the third closure member 26. As discussed above, the second fastener strip 36 may be attached to the support member 37 which is attached to the neck portion 18 generally longitudinally above the fourth closure member 28, such that the peripheral edge of the fourth member 28 with the rounded edges having a large radius 70, 72 overlaps the heat sealed, lower transversely extending edge of the support member 37.

Leakage performance test data for ostomy pouches including the closure system in accordance with the present disclosure indicates that the ostomy pouches including the closure system in accordance with the present disclosure provide improved seal capability with a lower risk of leakage when compared to pouches equipped with prior closure systems.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A drainable ostomy pouch, comprising:
a bodyside wall and an outer wall joined along their peripheral edges to define a cavity therebetween for collecting stomal discharge;
a downwardly extending neck portion terminating in a discharge opening for draining stomal discharge contents collected in the cavity, the neck portion including a closure system comprising:
a first closure member;
a second closure member, wherein the first closure member and the second closure member are arranged on opposite sides of the neck portion;
a third closure member arranged adjacent to the second closure member, such that the first closure member, the second closure member, and the third closure members are stacked on top of each other after the neck portion is folded once;
a fourth closure member arranged longitudinally offset from the third closure member; and
a two-part fastening system including a first fastener strip and a second fastener strip, wherein the first, second, third and fourth closure members are not fastener strips and do not interlock or adhere to each other.

2. The drainable ostomy pouch of claim 1, wherein each of the first closure member and the second closure member is curved smoothly and outwardly relative to the neck portion, such that the discharge opening remains open when neck portion is in a rolled-out position.

3. The drainable ostomy pouch of claim 2, wherein the third closure member is curved smoothly and outwardly relative to the neck portion.

4. The drainable ostomy pouch of claim 2, wherein the first closure member is attached on the bodyside wall of the neck portion and the second member is attached on the outer wall of the neck portion, wherein the first closure member and the second closure member are arranged in a back-to-back relation proximate the discharge opening.

5. The drainable ostomy pouch of claim 4, wherein the fourth closure member is curved smoothly and outwardly relative to the neck portion.

6. The drainable ostomy pouch of claim 4, wherein the fourth closure member is attached on the outer wall of the neck portion and longitudinally above the third closure member relative to the discharge opening, wherein the third closure member and the fourth closure member are spaced apart with a gap therebetween.

7. The drainable ostomy pouch of claim 6, wherein a longitudinal width of the gap is equal to or greater than a longitudinal width of the first, second or third closure member, whichever is largest.

8. The drainable ostomy pouch of claim 6, wherein the first fastener strip is attached on the bodyside wall of the neck portion opposite the gap between the third and fourth closure members.

9. The drainable ostomy pouch of claim 1, wherein the second fastener strip is disposed on the outer wall of the neck portion and longitudinally above the fourth closure member relative to the discharge opening, such that the first, second, third closure members and the first fastener strip are arranged along the neck portion between the second fastener strip and the discharge opening.

10. The drainable ostomy pouch of claim 1, wherein the second fastener strip is arranged on a support member formed of a polymeric film, a portion of which is heat sealed to the outer wall of the neck portion.

11. The drainable ostomy pouch of claim 10, wherein the fourth closure member is adhesively attached to the outer wall of the neck portion, such that a transversely extending edge of the fourth closure member overlaps the heat sealed portion of the support member.

12. The drainable ostomy pouch of claim 1, wherein the neck portion including the closure system is configured to be folded three times and sealed with the two-part fastening system.

13. The drainable ostomy pouch of claim 1, wherein the neck portion including the closure system is configured such that the second closure member and the third closure member directly abut each other after the neck portion is folded once, and the first, second, and third closure members are stacked on top of each other.

14. The drainable ostomy pouch of claim 13, wherein the neck portion including the closure system is configured such that the first fastener strip, the first closure member, the second closure member, and the third closure member are stacked on top of each other after the neck portion is folded twice.

15. The drainable ostomy pouch of claim 14, wherein the neck portion including the closure system is configured such that the first closure member, the second closure member, the third closure member, the fourth closure member, and the first fastener strip are stacked on top of each other after the neck portion is folded three times.

16. A closure system for a drainable ostomy pouch including generally parallel sidewalls of flexible sheet material joined along their peripheral edges to define a cavity therebetween for collecting stomal discharge and having a downwardly extending neck portion terminating in a discharge opening, the closure system arranged on the neck portion and comprising:

a first closure member;

a second closure member;

a third closure member;

a fourth closure member; and a two-part fastening system including a first fastener strip and a second fastener strip;

wherein the first closure member, the second closure member, the third closure member, the fourth closure member, and the first fastener strip are arranged along the neck portion longitudinally between the second fastener strip and the discharge opening, and the closure system is configured such that the neck portion is rolled up by folding three times and closed using the two-part fastening system, wherein the first, second, third and fourth closure members are not fastener strips and do not interlock or adhere to each other.

17. The closure system of claim 16, wherein the first closure member and the second closure member are attached to different sidewalls of the neck portion and arranged in a back-to-back relation, and wherein the third closure member is arranged longitudinally offset from the first closure member and the second closure member with a gap therebetween.

18. The closure system of claim 16, wherein the fourth closure member is arranged longitudinally offset from the second closure member with a gap therebetween, and the gap having a longitudinal width greater than the longitudinal width of the first, second and third closure members.

19. The closure system of claim 16, wherein the second closure member and the third closure member directly abut each other when the neck portion is rolled up and closed with the two-part fastening system.

* * * * *

UNITED STATES PATENT AND TRADEMARK OFFICE
CERTIFICATE OF CORRECTION

PATENT NO. : 9,011,395 B2
APPLICATION NO. : 13/827997
DATED : April 21, 2015
INVENTOR(S) : Friske et al.

It is certified that error appears in the above-identified patent and that said Letters Patent is hereby corrected as shown below:

IN THE SPECIFICATION

Column 1, lines 16-17, "ileostonty" to read as --ileostomy--.

Column 1, line 27, "as" to read as --a--.

Column 1, line 29, "draining," to read as --draining--.

Column 1, line 58, "fluffier" to read as --further--.

Column 2, line 13, "and," to read as --and--.

Column 3, line 7, "lust" to read as --first--.

Column 3, line 10, "Alter" to read as --After--.

Column 3, line 13, "to" to read as --top--.

Column 3, line 59, "drawings" to read as --drawings,--.

Column 4, line 15, "curved," to read as --curved--.

Column 4, line 37, "cavil" to read as --cavity--.

Column 4, line 40, "alter" to read as --after--.

Signed and Sealed this
Twenty-fourth Day of November, 2015

Michelle K. Lee
*Director of the United States Patent and Trademark Office*